United States Patent
Deimund et al.

(10) Patent No.: US 11,352,571 B2
(45) Date of Patent: Jun. 7, 2022

(54) OLIGOMERIZATION OF OLEFINS DERIVED FROM OXYGENATES

(71) Applicant: ExxonMobil Technology and Engineering Company, Annandale, NJ (US)

(72) Inventors: Mark A. Deimund, Jersey City, NJ (US); Brandon J. O'Neill, Lebanon, NJ (US); Ajit B. Dandekar, The Woodlands, TX (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 0 days.

(21) Appl. No.: 16/524,565

(22) Filed: Jul. 29, 2019

(65) Prior Publication Data

US 2020/0056106 A1    Feb. 20, 2020

Related U.S. Application Data

(60) Provisional application No. 62/718,643, filed on Aug. 14, 2018.

(51) Int. Cl.
*C10G 50/02* (2006.01)
*C07C 1/20* (2006.01)
(Continued)

(52) U.S. Cl.
CPC ............ *C10G 50/02* (2013.01); *B01J 29/703* (2013.01); *B01J 29/7261* (2013.01); *C07C 1/20* (2013.01);
(Continued)

(58) Field of Classification Search
CPC ............................ C10G 50/02; B01J 29/7261
See application file for complete search history.

(56) References Cited

U.S. PATENT DOCUMENTS 3,354,078 A    11/1967    Miale et al.
3,702,886 A    11/1972    Argauer et al.
(Continued)

FOREIGN PATENT DOCUMENTS

WO    2007135052 A1    11/2007
WO    2012039838 A2    3/2012

OTHER PUBLICATIONS

International Search Report and Written Opinion issued in related Application No. PCT/US2019/043863, dated Oct. 7, 2019 (24 pages).
(Continued)

*Primary Examiner* — Philip Y Louie
*Assistant Examiner* — Alyssa L Cepluch (57) ABSTRACT

Systems and methods are provided for conversion of oxygenate feeds to lubricant and/or distillate boiling range compounds with desirable properties by first selectively converting oxygenates to light olefins and then converting the light olefins to distillate and lubricant boiling range compounds with beneficial properties. The distillate boiling range products can have an unexpectedly high cetane, while the lubricant boiling range products can have an unexpectedly high viscosity index. The ability to form the distillate boiling range products and lubricant boiling range products is facilitated by using a Ni-enhanced oligomerization catalyst.

17 Claims, 2 Drawing Sheets

(51) Int. Cl.
*B01J 29/72* (2006.01)
*B01J 29/70* (2006.01)
*C10G 3/00* (2006.01)

(52) U.S. Cl.
CPC ....... *C10G 3/49* (2013.01); *C10G 2300/1088* (2013.01); *C10G 2300/70* (2013.01); *C10G 2400/10* (2013.01)

(56) References Cited

U.S. PATENT DOCUMENTS

| | | |
|---|---|---|
| 3,709,979 A | 1/1973 | Chu |
| 3,960,978 A | 6/1976 | Givens et al. |
| 4,021,502 A | 5/1977 | Plank et al. |
| RE29,948 E | 3/1979 | Dwyer et al. |
| 4,150,062 A | 4/1979 | Garwood et al. |
| 4,211,640 A | 7/1980 | Garwood et al. |
| 4,227,992 A | 10/1980 | Garwood et al. |
| 4,413,153 A | 11/1983 | Garwood et al. |
| 4,430,516 A | 2/1984 | La Pierre et al. |
| 4,433,185 A | 2/1984 | Tabak et al. |
| 4,542,247 A | 9/1985 | Chang et al. |
| 4,579,995 A | 4/1986 | Mauldin |
| 4,582,815 A | 4/1986 | Bowes |
| 4,717,782 A * | 1/1988 | Garwood ............... C07C 2/12 585/255 |
| 4,720,600 A | 1/1988 | Beech, Jr. et al. |
| 4,777,316 A | 10/1988 | Harandi et al. |
| 4,849,186 A | 7/1989 | Beech, Jr. et al. |
| 4,899,002 A | 2/1990 | Harandi et al. |
| 4,929,780 A | 5/1990 | Wright et al. |
| 5,043,499 A | 8/1991 | Harandi et al. |
| 5,146,032 A | 9/1992 | Harandi |
| 5,177,279 A | 1/1993 | Harandi |
| 5,453,555 A * | 9/1995 | Chang ..................... C07C 2/864 585/446 |
| 6,953,767 B2 | 10/2005 | Janssen et al. |
| 9,090,525 B2 | 7/2015 | Brown |
| 9,663,416 B2 | 5/2017 | Lilga et al. |
| 2004/0116757 A1 | 6/2004 | Van Egmond et al. |
| 2008/0257783 A1 | 10/2008 | Knottenbelt et al. |
| 2011/0147263 A1 | 6/2011 | Umansky et al. |
| 2011/0152594 A1 | 6/2011 | Brown |
| 2012/0004481 A1* | 1/2012 | Guillon .................. C10G 3/62 585/315 |
| 2012/0197053 A1 | 8/2012 | Cantrell et al. |
| 2014/0135552 A1 | 5/2014 | Nicholas et al. |
| 2017/0121237 A1* | 5/2017 | Ilias ........................ B01J 8/04 |
| 2017/0327437 A1 | 11/2017 | Hwang et al. |
| 2018/0170825 A1 | 6/2018 | O'Neill et al. |
| 2020/0055797 A1 | 2/2020 | Deimund et al. |
| 2020/0056106 A1 | 2/2020 | Deimund et al. |

OTHER PUBLICATIONS

Lacarriere et al., "Distillate-Range Products from Non-Oil-Based Sources by Catalytic Cascade Reactions", ChemSusChem, 5, 2012, 1787-1792.

Weisz et al., "Superactive Crystalline Aluminosilicate Hydrocarbon Catalysts", Journal of Catalysis, 4, 1965, 527-529.

Miale et al., "Catalysis by Crystalline Aluminosilicates IV. Attainable Catalytic Cracking Rate Constants, and Superactivity", Journal of Catalysis, 6, 1966, 278-287.

Olson et al., "Chemical and Physical Properties of the ZSM-5 Substitutional Series", Journal of Catalysis, 61, 1980, 390-396.

* cited by examiner

OLIGOMERIZATION OF OLEFINS DERIVED FROM OXYGENATES

CROSS-REFERENCE TO RELATED APPLICATIONS

This application claims priority to U.S. Provisional Application No. 62/718,643 filed Aug. 14, 2018, which is herein incorporated by reference in its entirety.

FIELD

This invention relates to integrated processes for forming lubricants, fuels, and/or chemicals by oligomerization of olefins formed by conversion of oxygenates.

BACKGROUND

An increasing number of hydrocarbon sources correspond to sources of methane and/or sources that are typically converted to small hydrocarbons to make the hydrocarbons suitable for further processing. One example is the increasing availability of natural gas. Natural gas typically includes a substantial portion of methane. While methane can be difficult to convert directly into products having larger carbon chains, processes for conversion of methane to methanol correspond to mature and widely used technologies. Similarly, processes are also available for conversion of coal and biomass to methane and/or methanol. Based on the increasing availability of these hydrocarbon sources, and the available methods for converting these sources to methanol, it would be beneficial to identify additional systems and methods for conversion of methanol to larger hydrocarbon products. In particular, it would be beneficial to identify conversion methods to allow methanol feeds to be used for higher value products, such as distillate fuels with high cetane ratings and/or lubricant boiling range products with high viscosity index values.

A variety of industrial processes are known for conversion of low boiling oxygenate compounds to higher value products. For example, methanol to gasoline (MTG) is a commercial process that produces gasoline from methanol using ZSM-5 catalysts. In the MTG process, methanol is first dehydrated to dimethyl ether. The methanol and/or dimethyl ether then react in a series of reactions that result in formation of aromatic, paraffinic, and olefinic compounds. The resulting product consists of liquefied petroleum gas (LPG) and a high-quality gasoline comprised of aromatics, paraffins, and olefins. The typical MTG hydrocarbon product consists of about 40-50% aromatics plus olefins and about 50-60% paraffins.

Another type of oxygenate conversion process can correspond to conversion of oxygenates to light olefins. An advantage of forming light olefins from methanol is that the light olefins can potentially be used in further oligomerization reactions. Unfortunately, the mixtures of light olefins produced by conventional methanol to olefin processes can differ from the types of light olefin mixtures that are preferred for oligomerization. Additionally, conventional conversion reactions for conversion of oxygenates to olefins can also tend to make substantial amounts of aromatics and paraffins. This combination of difficulties can be challenging when the desired goal of oligomerization is to form distillate fuel and/or lubricant boiling range compounds with desirable properties.

U.S. Pat. No. 4,899,002 describes a process for conversion of oxygenates to olefinic gasoline by first converting oxygenates to olefins in the presence of a zeolitic catalyst, and then converting olefins to gasoline and distillate fuels in the presence of a zeolitic catalyst.

U.S. Pat. No. 5,043,499 describes a process for fluid bed oligomerization of olefins. The process can include using at least two fluidized olefin oligomerization reaction zones operating in parallel, with one reaction zone operating under high severity reaction conditions that are effective for conversion of ethene.

U.S. Patent Application Publication No. 2012/0197053 describes conversion of olefins to liquid hydrocarbons using a two-stage oligomerization process. The first oligomerization stage includes a nickel-activated solid acid catalyst, while the second oligomerization stage includes a solid acid catalyst.

U.S. Patent Application Publication No. 2017/0327437 describes a two-stage process for oligomerization of ethylene. The first stage includes an Ni-containing mesoporous catalyst while the second stage includes a solid acid catalyst.

U.S. Pat. No. 9,663,416 describes methods for conversion of ethylene-containing feeds to distillate fuels by oligomerization. The ethylene-containing feed can be formed from a renewable oxygenate source, such as renewable ethanol.

U.S. Pat. No. 9,090,525 describes conversion of oxygenates in the presence of a zeolitic catalyst to form olefins, and then converting the olefins in the presence of a zeolitic catalyst to form naphtha boiling range compounds with increased octane. In one aspect, a portion of the naphtha boiling range olefins from an initial conversion product are recycled to the oxygenate conversion process to allow for formation of heavier naphtha boiling range compounds, including aromatics.

SUMMARY

In various aspects, a method for conversion of oxygenates is provided. The method can include exposing a feed comprising one or more oxygenates to an oxygenate conversion catalyst under conditions for producing an olefin-containing effluent. The olefin-containing effluent can include 60 wt % or more of $C_3$-$C_6$ olefins and/or 10 wt % or less aromatics relative to a weight of hydrocarbons in the olefin-containing effluent. Optionally, a ratio of $C_5$-$C_6$ olefins versus $C_4$ olefins in the olefin-containing effluent can be 1.0 or more. Optionally, the olefin-containing effluent comprises 40 wt % or more of $C_4$-$C_6$ olefins. The methanol conversion catalyst can include a zeotype framework structure having a largest pore channel corresponding to a 10-member ring pore channel. A light olefin effluent can be separated from the olefin-containing effluent, such as a light olefin effluent including 70 wt % or more total olefins relative to a weight of hydrocarbons in the light olefin effluent. At least a portion of the light olefin effluent can then be exposed to an oligomerization catalyst comprising Ni supported on a support comprising a zeotype framework structure having 1-D 10-member ring pore channels under oligomerization conditions to form an oligomerized effluent. The at least a portion of the light olefin effluent can include 5.0 wt % or more ethylene relative to a weight of olefins in the at least a portion of the light olefin effluent. Optionally, the oligomerization conditions can correspond to conditions for conversion of 50 wt % or more of the ethylene in the at least a portion of the light olefin effluent.

Optionally, exposing at least a portion of the olefin-containing effluent to an oligomerization catalyst can correspond to exposing portions of the olefin-containing effluent to a series of oligomerization catalyst. For example, at least a portion of the light olefin effluent can be exposed to a first oligomerization catalyst comprising a solid acid catalyst having zeotype framework structure under first oligomerization conditions to form a first oligomerized effluent. The at least a portion of the light olefin effluent can include 10 wt % or more ethylene relative to a weight of olefins in the at least a portion of the light olefin effluent. Additionally or alternately, a weight of $C_2$ olefins in the first oligomerized effluent can be 50 wt % or more of a weight of $C_2$ olefins in the light olefin effluent. At least a portion of the first oligomerized effluent can then be exposed to a second oligomerization catalyst comprising Ni supported on a support comprising a zeotype framework structure having 1-D 10-member ring pore channels under second oligomerization conditions to form a second oligomerized effluent. The second oligomerization conditions can correspond to conditions for conversion of 50 wt % or more of the ethylene in the at least a portion of the first oligomerization effluent.

DETAILED DESCRIPTION

All numerical values within the detailed description and the claims herein are modified by "about" or "approximately" the indicated value, and take into account experimental error and variations that would be expected by a person having ordinary skill in the art.

Overview

In various aspects, systems and methods are provided for conversion of oxygenate feeds to lubricant and/or distillate boiling range compounds with desirable properties by first selectively converting oxygenates to light olefins and then converting the light olefins to distillate and lubricant boiling range compounds with beneficial properties. The distillate boiling range products can have an unexpectedly high cetane, while the lubricant boiling range products can have an unexpectedly high viscosity index.

Conventionally, methanol conversion catalysts such as ZSM-5 have traditionally been favored for conversion of methanol. Such methanol catalysts have higher selectivity for formation of aromatic compounds. This increased selectivity for formation of aromatics has traditionally been viewed as beneficial, since any aromatics formed during methanol conversion represent components that can have higher value with little or no additional processing.

In contrast to conventional methods, it has been unexpectedly discovered that it can be beneficial to convert oxygenates (such as methanol and/or dimethyl ether) to an olefinic mixture that includes a reduced or minimized amount of aromatics while also being selective for formation of light olefins. For example, oxygenate conversion catalysts such as EMM-2 can be beneficial for converting a methanol-containing feed (or another oxygenate-containing feed) to form an oxygenate conversion effluent composed primarily of $C_2$ and $C_3$ olefins. Other oxygenate conversion catalysts, such as ZSM-48, can be beneficial for forming an oxygenate conversion effluent composed primarily of $C_2$ to $C_6$ olefins.

Additionally, in some aspects the oxygenate conversion catalyst can be beneficial for forming a methanol conversion effluent that includes 10 wt % or less aromatics, or 6 wt % or less.

After the selective conversion of oxygenates to light olefins, a separation can be performed to separate a stream enriched in the light olefins from one or more remaining portions of the conversion effluent. The light olefins can then be used as the input for an oligomerization catalyst to form oligomerized product that includes diesel and/or lubricant boiling range components. The resulting diesel and/or lubricant boiling range components formed by this method can have unexpectedly beneficial properties, such as increased cetane value and/or increased viscosity index. In various aspects, at least a portion of the oligomerization catalyst can correspond to a catalyst including a zeotype framework structure with a 1-D 10-member ring pore channel as the large pore channel in the framework structure. ZSM-48 is an example of a suitable zeotype framework structure. The catalyst can further include a supported metal, such as Ni, Co, or optionally another Group 8-10 metal.

Without being bound by any particular theory, it is believed that the unexpectedly improved properties of the distillate fuel and/or lubricant boiling range components can be due in part to using an olefinic feed with a reduced or minimized concentration of larger olefins and/or other components. Additionally or alternately, without being bound by any particular theory, it is believed that the unexpectedly improved properties of the distillate fuel and/or lubricant boiling range components can be due in part tousing an oligomerization catalyst that includes Ni (or optionally Co or another Group 8-10 metal) supported on a zeotype framework structure having a 1-D 10-member ring pore channel as the largest pore channel. Still further unexpected improvements may be due to use of an oxygenate feed substantially composed of oxygenates containing only $C_1$ alkyl groups, such as methanol and dimethyl ether. This combination of features can allow for selective production of desired light olefins, with the light olefins being selectively oligomerized into aliphatic compounds with a reduced or minimized amount of branching. The ability to produce larger oligomers with selectivity for forming aliphatic compounds with reduced or minimized branching can be beneficial for unexpectedly increasing the cetane value of the resulting distillate fuel boiling range portion of the oligomerization effluent. Additionally or alternately, the larger oligomers can still have branches that correspond primarily to methyl and/or ethyl branches. This limited amount of methyl and ethyl branching can result in an unexpectedly high viscosity index for the lubricant boiling range portion of the oligomerization effluent.

An additional difficulty with conversion of oxygenates to naphtha boiling range products can be related to the tendency for the catalyst to deactivate relatively quickly. In various aspects, the systems and methods described herein can be beneficial for reducing or minimizing the amount of coke formation on the oligomerization catalyst and/or reducing or minimizing any deactivation of the oligomerization catalyst. In particular, it has been unexpectedly discovered that using Ni (or optionally Co or another metal) supported on a zeotype framework structure comprising a 1-D 10-member ring pore channel can be beneficial for reducing or minimizing deactivation of the oligomerization catalyst.

In this discussion, the naphtha boiling range is defined as 50° F. (~10° C., roughly corresponding to the lowest boiling point of a pentane isomer) to 350° F. (177° C.). The distillate fuel boiling range, is defined as 350° F. (177° C.) to ~680°

F. (360° C.). The lubricant boiling range is defined as 360° C. to 538° C. Because the oligomerization effluents described herein will typically not include compounds with a boiling point greater than 538° C., the lubricant boiling range can alternatively be referred to as a 538° C.+ portion of an oligomerization effluent. Compounds ($C_{4-}$) with a boiling point below the naphtha boiling range can be referred to as light ends. It is noted that due to practical consideration during fractionation (or other boiling point based separation) of hydrocarbon-like fractions, a fuel fraction formed according to the methods described herein may have T5 and T95 distillation points corresponding to the above values (or T10 and T90 distillation points), as opposed to having initial/final boiling points corresponding to the above values. While various methods are available for determining boiling point information for a given sample, for the claims below ASTM D2887 is a suitable method for determining distillation points (including fractional weight distillation points) for a composition.

In this discussion, amounts of feed conversion and amounts of product yield are provided based on once-through operation for the olefin-containing feed to produce distillates and/or lubricants, unless otherwise specified.

In various aspects, a conversion catalyst including a suitable zeotype framework material (such as a zeolitic material) can be used for conversion of oxygenate feeds to naphtha boiling range fractions and olefins. In various aspects, an optionally transition metal-enhanced zeotype catalyst composition, such as a catalyst composition including an Ni-enhanced zeotype framework material, can be used for oligomerization of olefins generated during conversion of an oxygenate feed for formation of distillate boiling range fractions. In this discussion and the claims below, a zeotype is defined to refer to a crystalline material having a porous framework structure built from tetrahedra atoms connected by bridging oxygen atoms. Examples of known zeotype/zeolite frameworks are given in the "Atlas of Zeolite Frameworks" published on behalf of the Structure Commission of the International Zeolite Association", $6^{th}$ revised edition, Ch. Baerlocher, L. B. McCusker, D. H. Olson, eds., Elsevier, New York (2007) and the corresponding web site, http://www.iza-structure.org/databases/. Under this definition, a zeolite can refer to aluminosilicates having a zeotype framework type as well, while a zeotype more generally refers crystalline structures having a suitable framework structure that may contain oxides of Si, Al, and/or heteroatoms different from Si and Al. Such heteroatoms can include any heteroatom generally known to be suitable for inclusion in a zeotype framework, such as gallium, boron, germanium, phosphorus, zinc, and/or other transition metals that can substitute for silicon and/or aluminum in a zeotype framework.

In this discussion, reference is made to the ring size of the pore channels of a material having a zeotype framework structure. One option for characterizing the ring size is based on the number of atoms in the ring structure that defines the largest pore channel in the zeotype framework structure. For example, a material having a ZSM-48 framework type includes 10-member ring pore channels as the largest pore channels. The 10-member ring pore channels in a ZSM-48 framework structure correspond to 1-dimensional (or 1-D) pore channels.

In this discussion, a $C_x$ hydrocarbon, alcohol, olefin, oxygenate, or other compound, or of a carbon chain in such a compound, is a reference to a compound (or carbon chain in such a compound) that contains the specified number of carbons. Methanol is an example of a $C_1$ alcohol. Dimethyl ether is an example of an ether containing two $C_1$ carbon chains. A reference to a stream or fraction containing $C_x$-$C_y$ compounds corresponds to a stream or fraction that contains at least one component having a carbon backbone with x carbons, y carbons, or a number of carbons between x and y. For example, a stream containing $C_3$-$C_6$ olefins corresponds to a stream containing at least one of $C_3$ olefins, $C_4$ olefins, $C_5$ olefins, or $C_6$ olefins.

In this discussion, cetane index can be determined using ASTM D4737. Viscosity index can be determined using ASTM D2270.

Feedstocks and Products—Oxygenate Conversion

In various aspects, catalysts described herein can be used for conversion of oxygenate feeds to oligomerized products via an initial conversion to a small olefin intermediate product. Examples of oxygenates can include oxygenates containing at least one $C_1$-$C_4$ alkyl group and/or other oxygenates. Preferably, the oxygenates can correspond to oxygenates that include $C_1$ alkyl groups. In this discussion, methanol is an oxygenate that corresponds to an alcohol that includes a $C_1$ alkyl group. Dimethyl ether (DME) is an oxygenate that corresponds to an ether that includes $C_1$ alkyl groups. Examples of suitable oxygenates include feeds containing methanol, dimethyl ether, $C_1$-$C_4$ alcohols, ethers with $C_1$-$C_4$ alkyl chains, including both asymmetric ethers containing $C_1$-$C_4$ alkyl chains (such as methyl ethyl ether, propyl butyl ether, or methyl propyl ether) and symmetric ethers (such as diethyl ether, dipropyl ether, or dibutyl ether), or combinations thereof. It is noted that oxygenates containing at least one $C_1$-$C_4$ alkyl group are intended to explicitly identify oxygenates having alkyl groups containing 4 carbons or less. Preferably the oxygenate feed can include 30 wt % or more of one or more suitable oxygenates, or 50 wt % or more, or 75 wt % or more, or 90 wt % or more, or at least 95 wt %. Additionally or alternately, the oxygenate feed can include 50 wt % or more methanol and/or DME, or 75 wt % or more methanol and/or DME, or 90 wt % or more methanol and/or DME, or 95 wt % methanol and/or DME. In particular, the oxygenate feed can include 30 wt % to 100 wt % of oxygenate (such as methanol and/or DME), or 50 wt % to 95 wt %, or 75 wt % to 100 wt %, or 75 wt % to 95 wt %. The oxygenate feed can be derived from any convenient source. For example, the oxygenate feed can be formed by reforming of hydrocarbons in a natural gas feed to form synthesis gas ($H_2$, CO, $CO_2$), and then using the synthesis gas to form methanol (or other alcohols).

In addition to oxygenates, a feed can also include diluents, such as water (in the form of steam), nitrogen or other inert gases, and/or paraffins or other non-reactive hydrocarbons. Optionally, at least a portion of such diluents can be removed prior to exposing the methanol (or other oxygenate feed) to a conversion catalyst. Optionally, the feed can further include olefins, such as 10 wt % or less of olefins, or 5 wt % or less. Such optional olefins can, for example, correspond to $C_2$-$C_6$ olefins, such as having 70 wt % or more of the olefins correspond to $C_2$-$C_3$ olefins, or such as having 50 wt % or more of the olefins correspond to $C_3$-$C_6$ olefins. In such optional aspects, 10 wt % or less of the olefins can correspond to $C_{7+}$ olefins, or 5 wt % or less, or 1 wt % or less.

In various aspects, a first step in the process for forming oligomerized products can be to convert methanol (and/or other oxygenates) into small olefins that are suitable for oligomerization. The methanol can be converted in the presence of a conversion catalyst under oxygenate conversion conditions. In some aspects, the oxygenate conversion reaction can be performed using a catalyst including an MRE framework structure and/or a zeotype framework structure including a 10-member, 1-D pore channel as the largest pore channel in the framework structure. Examples of MRE framework structure materials include ZSM-48, EU-2, EU-11, and ZBM-30. Other examples of framework structures including a 10-member, 1-D pore channel include TON (Theta-1, ZSM-22) and MTT (ZSM-23). Still another suitable framework structure is ZSM-12 (MTW), although ZSM-12 has a 12-member, 1-D pore channel. In such aspects, the yield of aromatics relative to the total hydrocarbons in the conversion product can be 0.1 wt % to 20 wt %, 0.5 wt % to 10 wt %, or 1 wt % to 6 wt %. Additionally or alternately, the yield of olefins relative to the total hydrocarbons in the conversion product can be 20 wt % to 95 wt %, or 20 wt % to 90 wt %, or 30 wt % to 90 wt %, or 40 wt % to 90 wt %, or 50 wt % to 90 wt %, or 20 wt % to 80 wt %, or 30 wt % to 80 wt %, or 20 wt % to 70 wt %, or 20 wt % to 60 wt %, or 20 wt % to 50 wt %. Further additionally or alternately, the yield of paraffins relative to the total hydrocarbon product can be 10 wt % to 50 wt %, or 20 wt % to 40 wt %. For the paraffins and olefins generated during oxygenate conversion, 50 wt % or more of the olefins can correspond to $C_3$ and $C_4$ olefins (relative to a total weight of olefins) and/or 50 wt % or more of the paraffins can correspond to $C_3$ and $C_4$ paraffins (relative to a total weight of paraffins). Additionally or alternately, 60 wt % or more of the olefins can correspond to $C_3$ to $C_6$ olefins (or 70 wt % or more, or 80 wt % or more), and/or 60 wt % or more of the hydrocarbons in the conversion effluent can correspond to $C_3$ to $C_6$ olefins (or 70 wt % or more, or 80 wt % or more). Additionally or alternately, a ratio of $C_5$-$C_6$ olefins versus $C_4$ olefins in the conversion effluent can be 1.0 or more, or 1.2 or more, or 1.4 or more, such as up to 2.0 or possibly still higher. Further additionally or alternately, 40 wt % or more of the hydrocarbons in the conversion effluent can correspond to $C_4$-$C_6$ olefins, or 50 wt % or more. Further additionally or alternately, less than 10 wt % of the paraffins can correspond to $C_1$ paraffins (methane). In the claims below, the relative amounts of paraffins, olefins, and aromatics in a sample can be determined based on ASTM D6839.

In some aspects, the oxygenate conversion reaction can be performed using a catalyst including an EMM-2 framework structure (intergrowth structure of AEI and CHA framework types) and/or a zeotype framework structure corresponding to an integrowth structure of two or more zeotype framework materials each having a 8-member pore channel as the largest pore channel in the framework structure. Optionally, the two or more materials having a 8-member pore channel as the largest pore channel can each have 8-member ring 3-D pore channels. Other suitable catalysts can include a CHA framework structure, such as SAPO-34, a AEI framework structure, or an EMM-4 framework structure. In such aspects, the yield of aromatics relative to the total hydrocarbons in the conversion product can be 0 wt % to 10 wt %, or 0.5 wt % to 10 wt %, or 1 wt % to 6 wt %. Additionally or alternately, the yield of olefins relative to the total hydrocarbons in the conversion product can be 20 wt % to 100 wt %, or 30 wt % to 100 wt %, or 40 wt % to 100 wt %, or 50 wt % to 100 wt %, or 20 wt % to 90 wt %, or 30 wt % to 90 wt %, or 20 wt % to 80 wt %, or 20 wt % to 70 wt %, or 20 wt % to 60 wt %, or 20 wt % to 50 wt %. Further additionally or alternately, the yield of paraffins relative to the total hydrocarbon product can be 0 wt % to 50 wt %, or 0.5 wt % to 50 wt %, or 10 wt % to 50 wt %, or 20 wt % to 40 wt %.

For the olefins generated during oxygenate conversion, 70 wt % or more of the olefins, or 80 wt % or more, such as up to substantially all of the olefins can correspond to $C_2$ and $C_3$ olefins, relative to a total weight of olefins. Additionally or alternately, a ratio of $C_3$ olefins to $C_2$ olefins generated during oxygenate conversion can be 3.0 or less, or 2.5 or less, or 2.0 or less, such as down to 0.5 or possibly still lower. For the paraffins generated during oxygenate conversion, 70 wt % or more of the paraffins (such as up to substantially all) can correspond to $C_2$ and $C_3$ paraffins, relative to a total weight of paraffins. Further additionally or alternately, less than 10 wt % of the paraffins can correspond to $C_1$ paraffins (methane). Still further additionally or alternately, 30 wt % or more of the olefins can be $C_2$ olefins (i.e., ethylene), or 40 wt % or more, or 50 wt % or more, or 60 wt % or more, such as up to 80 wt % or possibly still higher.

The conversion conditions can also result in generation of some naphtha boiling range components, CO, and/or $CO_2$. In some aspects, the amount of combined CO, $CO_2$, and $CH_4$ can correspond to ~6.0 wt % or less of the total hydrocarbon product in a conversion effluent, or ~5.0 wt % or less. In this discussion and the claims below, the amounts of CO and $CO_2$ in a conversion effluent are included when determining the amount of the total hydrocarbon product (such as the weight of the total hydrocarbon product).

Suitable and/or effective conditions for performing a conversion reaction (for conversion of methanol or another oxygenate to olefins) can include average reaction temperatures of 300° C. to 550° C. (or 350° C. to 550° C., or 400° C. to 500° C.), total pressures between 10 psig (~70 kPa-g) to 400 psig (~2700 kPa-g), or 50 psig (~350 kPa-g) to 350 psig (~2400 kPa-g), or 100 psig (~700 kPa-g) to 300 psig (~2100 kPa-g), and an oxygenate space velocity between 0.1 $h^{-1}$ to 10 $h^{-1}$ based on weight of oxygenate relative to weight of catalyst. For example, the average reaction temperature can be at least 300° C., or at least 350° C., or at least 400° C., or at least 450° C. Additionally or alternately, the average reaction temperature can be 550° C. or less, or 500° C. or less, or 450° C. or less, or 400° C. or less. In this discussion, average reaction temperature is defined as the average of the temperature at the reactor inlet and the temperature at the reactor outlet for the reactor where the conversion reaction is performed. In some aspects where lower pressures are used, the pressure can correspond to 70 kPa-g to 700 kPa-g. As another example, the total pressure can be at least 70 kPa-g, or at least 350 kPa-g, or at least 500 kPa-g, or at least 700 kPa-g, or at least 1000 kPa-g. Additionally or alternately, the total pressure can be 3000 kPa-g or less, or 2700 kPa-g or less, or 2400 kPa-g or less, or 2100 kPa-g or less.

Various types of reactors can provide a suitable configuration for performing a conversion reaction (including an oligomerization reaction). Suitable reactors can include fixed bed reactors, moving bed reactors, and fluidized bed reactors (such as riser reactors). It is noted that the activity and/or selectivity of a catalyst for oxygenate conversion can vary as the catalyst is exposed to increasing amounts of oxygenate feed.

It is noted that the oxygenate feed and/or conversion reaction environment can include water in various proportions. Conversion of oxygenates to olefins results in production of water as a product, so the relative amounts of oxygenate (such as methanol) and water can vary within the reaction environment. Based on the temperatures present during methanol conversion, the water in the reaction environment can result in "steaming" of a catalyst. Thus, a catalyst used for conversion of oxygenates to aromatics is preferably a catalyst that substantially retains activity when steamed. Water may also be present in a feed prior to contacting the zeolite (or other zeotype) catalyst. For example, in commercial processing of methanol or bio-ethanol to form gasoline boiling range compounds, in order to control heat release within a reactor, an initial catalyst stage may be used to convert a portion of the methanol in a feed to dimethyl ether and water prior to contacting a zeolite catalyst for forming gasoline.

Feedstock and Products—Olefin Oligomerization

In various aspects, catalysts described herein can be used for oligomerization of olefin-containing feeds generated by conversion of methanol (and/or other oxygenates) to form heavier molecular weight and/or higher boiling products. Examples of oligomerized products can include products in the distillate fuel boiling range and the lubricant boiling range. An oligomerization process suitable for forming distillate fuel boiling range products can often also form naphtha boiling range products and lubricant boiling range products (i.e., 360° C.+ products).

After formation of a conversion effluent as described above, the conversion effluent can optionally be separated to form an olefin-containing feed. For example, one or more separations can be performed on the conversion effluent (or a portion thereof) to separate water, CO, and $CO_2$ from the desired olefin-containing feed. Additionally or alternatively, one or more separations can be performed on the conversion effluent (or a portion thereof) to remove heavier hydrocarbons, such as $C_{6+}$ aromatics and $C_{7+}$ aliphatics, from the desired olefin-containing feed. This can result in an olefin-containing feed where 30 wt % or more (such as up to substantially all) of the hydrocarbons in the feed can correspond to olefins, or 30 wt % to 90 wt %, or 40 wt % to 80 wt %, or 30 wt % to 70 wt %. Additionally or alternatively, depending on the catalyst, 10 wt % or more of the olefins can correspond to $C_2$ olefins (relative to a weight of the olefins), or 20 wt % or more, or 30 wt % or more, or 40 wt % or more, or 50 wt % or more, such as up to 90 wt % or possibly still higher. The distribution of olefins in the olefin-containing feed can be similar to the distribution in the conversion effluent as described above. For example, for a conversion effluent formed from a catalyst containing a zeotype framework such as ZSM-48, the resulting olefin-containing feed can include 60 wt % or more of $C_3$ to $C_6$ olefins relative to a weight of olefins in the olefin-containing feed, or 70 wt % or more, or 80 wt % or more. For a conversion effluent formed from a catalyst containing a zeotype framework such as EMM-2, the resulting olefin-containing feed can include 70 wt % or more of $C_2$ to $C_3$ olefins relative to a weight of olefins in the olefin-containing feed, or 80 wt % or more. In such aspects, after performing a separation to form an olefin-containing feed, the olefin-containing feed can optionally contain 10 wt % or less of $C_3$ olefins relative to the total weight of olefins in the olefin-containing feed, or 5.0 wt % or less, or 1.0 wt % or less.

The total hydrocarbon product in the oligomerization effluent can include (at least) a naphtha boiling range portion, a distillate fuel boiling range portion, and a 371° C.+ portion. In various aspects, the yield of a distillate fuel boiling range of the total hydrocarbon product can be 55 wt % to 75 wt % relative to the weight of olefins in the input to the oligomerization stage, or 55 wt % to 70 wt %, or 55 wt % to 65 wt %, or 60 wt % to 70 wt %. Additionally or alternatively, the selectivity for forming/yield of a naphtha boiling range portion can be 15 wt % to 35 wt %, or 15 wt % to 25 wt %. With regard to the lubricant boiling range fraction, the selectivity for forming/yield of 360° C.+ compounds can be 5 wt % to 25 wt %, or 10 wt % to 25 wt %.

It is noted that a portion of the total hydrocarbon product can correspond to unreacted olefins, such as unreacted ethylene. In some aspects, the amount of ethylene ($C_2$ olefins) remaining in the total hydrocarbon product can be 50 wt % or less of the amount of ethylene present in the olefin-containing feed, or 30 wt % or less, or 10 wt % or less, such as down to 0.1 wt % or possibly still lower. Additionally or alternatively, relative to the total hydrocarbon product, the amount of ethylene can be 0.1 wt % to 5.0 wt %, or 0.1 wt % to 1.5 wt %. In some aspects, the amount of $C_{3+}$ olefins remaining in the total hydrocarbon product can be 5.0 wt % or less of the amount of olefins in the total hydrocarbon product, or 1.0 wt % or less.

Optionally, at least a portion of the olefins (such as at least a portion of the $C_2$-$C_4$ olefins) from the total hydrocarbon product can be recycled for inclusion as part of the feed to the oliogmerization. Additionally or alternatively, at least a portion of the naphtha boiling range product can be recycled as part of the feed. This can be beneficial for increasing yields for the distillate fuel boiling range portion and/or the 371° C.+ portion. It is noted that in aspects involving recycle of a portion of the total hydrocarbon product, the amount of conversion in a single pass may be reduced in order to reduce or minimize the exotherm associated with oligomerization. In such aspects, the yield per pass for the distillate boiling range portion and/or 371° C.+ portion in the total hydrocarbon product may be toward the lower end of the range.

The distillate boiling range portion of the oligomerization effluent can have a cetane rating of 40 or more, or 42 or more, or 45 or more, or 47 or more, such as up to 52 or possibly still higher. It is noted that the cetane rating of the distillate boiling range portion can be dependent on the type of olefins formed in the oxygenate conversion step. Generally, oxygenate conversion steps that produce higher percentages of $C_2$ and/or $C_3$ olefins can result in higher cetane ratings. In some aspects, the distillate boiling range portion can be substantially free of aromatics, such as having an aromatics content of 1.0 wt % or less. Additionally or alternatively, the distillate boiling range portion can be substantially free of sulfur and/or nitrogen, such as having a sulfur content and/or a nitrogen content of 10 wppm or less, or 1 wppm or less. The lubricant boiling range portion of the oligomerization effluent (or a 360° C. to 455° C. portion of the oligomerization effluent) can have a viscosity index of 85 or more, or 90 or more, or 95 or more, or 105 or more, or 110 or more, such as up to 120 or possibly still higher. It is noted that the viscosity index of the lubricant boiling range portion can be dependent on the type of olefins formed in the oxygenate conversion step. Generally, oxygenate conversion steps that produce higher percentages of $C_2$ olefins can result in higher viscosity index ratings. In some aspects, the lubricant boiling range portion can also have a cetane rating greater than 50. Optionally, the lubricant boiling range portion can be fractionated to form a light neutral fraction and a heavy neutral fraction. The light neutral fraction can have a kinematic viscosity at 100° C. of 3.5 cSt to 4.5 cSt. In aspects where the olefin feed includes a higher proportion of $C_2$ and $C_3$ olefins, the light neutral fraction can have a viscosity index of 95 or more, or 105 or more, or 110 or more, such as up to 130 or possibly still higher. In aspects where the olefin feed includes a higher proportion of $C_3$ to $C_6$ olefins, the light neutral fraction can have a viscosity index of 90 to 110. The aromatics content of the distillate boiling range portion can be 1.0 wt % or less, or 0.5 wt % or less, as determined by ASTM D5186.

Because the oligomerization process described herein is selective for formation of compounds with reduced or minimized amounts of branching, the resulting naphtha boiling range portion of the oligomerized effluent can have a somewhat lower octane rating. In some aspects, the naphtha boiling range portion formed from an oligomerization process can have an octane rating of 75 or less, or 70 or less, such as down to 60 or possibly still lower. Due to the low octane rating, in some aspects it can be beneficial to recycle a portion of the naphtha boiling range portion for use as part of the feed to the oligomerization. Octane rating can be determined using (RON+MON)/2, with RON and MON determined according to ASTM D2699 and D2700, respectively. In some aspects, the naphtha boiling range portion can be substantially free of aromatics, such as having an aromatics content of 1.0 wt % or less. Additionally or alternately, the naphtha boiling range portion can be substantially free of sulfur and/or nitrogen, such as having a sulfur content and/or a nitrogen content of 10 wppm or less, or 1 wppm or less.

The oligomerization reaction can be performed in the presence of an oligomerization catalyst that includes an MRE framework structure (ZSM-48), an MFS framework structure (ZSM-57), a zeotype framework structure including a 10-member ring, 1-D pore channel as the largest pore channel in the framework structure, and/or a zeotype framework structure including a 10-member ring, 2-D pore channel as the largest pore channel. Examples of MRE framework structure materials include ZSM-48, EU-2, EU-11, and ZBM-30. Other examples of framework structures including a 10-member ring, 1-D pore channel include TON (Theta-1, ZSM-22) and MTT (ZSM-23). In aspects where the catalyst includes an MRE framework structure material, such as ZSM-48, the ZSM-48 (or other MRE material) can have a silica to alumina ratio of 50 to 180, or 60 to 100. It is noted that the molar ratio described herein is a ratio of silicon to aluminum. If a corresponding ratio of silica to alumina were described, the corresponding ratio of silica ($SiO_2$) to alumina ($Al_2O_3$) would be twice as large, due to the presence of two aluminum atoms in each alumina stoichiometric unit. Thus, a silicon to aluminum ratio of 10 corresponds to a silica to alumina ratio of 20.

Preferably, the oligomerization catalyst can include 0.1 wt % to 10 wt % of Ni as a supported metal, or 0.5 wt % to 2.0 wt %. The Ni can be added to the oligomerization catalyst by any convenient method, such as by spray coating, ion exchange, or incipient wetness.

In some aspects, the oligomerization catalyst can have an alpha value of less than 100. In some aspects, a zeolite (or other zeotype) in a catalyst can be present at least partly in the hydrogen form. Depending on the conditions used to synthesize the zeolite (or zeotype), this may correspond to converting the zeolite from, for example, the sodium form. This can readily be achieved, for example, by ion exchange to convert the zeolite to the ammonium form followed by calcination in air or an inert atmosphere at a temperature of 400° C. to 700° C. to convert the ammonium form to the active hydrogen form.

Alpha value is a measure of the acid activity of a zeolite catalyst (or other zeotype catalyst) as compared with a standard silica-alumina catalyst. The alpha test is described in U.S. Pat. No. 3,354,078; in the Journal of Catalysis, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the Journal of Catalysis, Vol. 61, p. 395. Higher alpha values correspond with a more active cracking catalyst.

The catalyst composition can employ the transition metal-enhanced zeolite (or other zeotype) in its original crystalline form or after formulation into catalyst particles, such as by extrusion. A process for producing zeolite extrudates in the absence of a binder is disclosed in, for example, U.S. Pat. No. 4,582,815, the entire contents of which are incorporated herein by reference. Preferably, the transition metal can be incorporated after formulation of the zeolite/zeotype (such as by extrusion) to form self-bound catalyst particles. Optionally, a self-bound catalyst can be steamed after extrusion. The terms "unbound" and "self-bound" are intended to be synonymous and mean that the present catalyst composition is free of any of the inorganic oxide binders, such as alumina or silica, frequently combined with zeolite catalysts to enhance their physical properties.

As an alternative to forming self-bound catalysts, zeolite crystals (or zeotype crystals) can be combined with a binder to form bound catalysts. Suitable binders for zeolite-based catalysts (or zeotype-based catalysts) can include various inorganic oxides, such as silica, alumina, zirconia, titania, silica-alumina, cerium oxide, magnesium oxide, yttrium oxide, or combinations thereof. Generally, a binder can be present in an amount between 1 wt % and 95 wt %, for example between 5 wt % and 40 wt % of a catalyst composition. In some aspects, the catalyst can include at least 5 wt % binder, or at least 10 wt %, or at least 20 wt %. Additionally or alternately, the catalyst can include 90 wt % or less of binder, or 50 wt % or less, or 40 wt % or less, or 35 wt % or less. Combining the zeolite (or zeotype) and the binder can generally be achieved, for example, by mulling an aqueous mixture of the zeolite and binder and then extruding the mixture into catalyst pellets. A process for producing zeolite extrudates using a silica binder is disclosed in, for example, U.S. Pat. No. 4,582,815. Optionally, a bound catalyst can be steamed after extrusion.

Suitable and/or effective conditions for performing an oligomerization reaction can include average reactor temperatures of 125° C. to 250° C. (or 125° C. to 200° C., or 150° C. to 220° C.); total pressures between 100 psig (~0.7 MPa-g) to 3000 psig (~20.7 MPa-g), or 100 psig (~0.7 MPa-g) to 2000 psig (~13.8 MPa-g), or 200 psig (~1.3 MPa-g) to 1000 psig (~6.9 MPa-g), or 70 psig (~500 kPa-g) to 180 psig (~1200 kPa-g); and an olefin space velocity between 0.1 $h^{-1}$ to 5 $h^{-1}$ based on weight of olefins relative to weight of catalyst. In some aspects, the lower pressure operating range for oligomerization can be beneficial for performing oligomerization on an olefin-containing portion of an oxygenate conversion effluent without having to perform prior compression on the portion of the conversion effluent. One option for selecting suitable oligomerization conditions can be to select conditions effective for conversion of a desired percentage of the ethylene within the feed to oligomerization. For example, the effective conditions for oligomerization can comprise conditions for conversion of 50 wt % or more of the ethylene in the feed to oligomerization, or 70 wt % or more, or 90 wt % or more.

Various types of reactors can provide a suitable configuration for performing an oligomerization reaction. Suitable reactors can include fixed bed reactors (such as trickle bed reactors), moving bed reactors, and fluidized bed reactors (such as riser reactors). In aspects where a catalyst can be removed from the reactor for regeneration and recycle during operation of the reactor, such as a moving bed reactor and/or fluidized bed reactor, catalyst can be removed and replaced with regenerated catalyst.

In some aspects, oligomerization can be performed in multiple stages. For example, a first oligomerization stage can be used to selectively react the $C_{3+}$ olefins in the feed. An (optional) separation can then be performed to remove oligomerized products from the remaining portion of the oligomerization feed. A second stage can then be used to form oligomers from the remaining portion of the oligomerization feed, which is enriched in $C_2$ olefins due to the selective reaction of heavier olefins in the first oligomerization stage.

In aspects where two or more oligomerization stages are used, the second stage catalyst can correspond to a catalyst including Ni supported on a framework structure corresponding to MRE, MFS, a structure with a 10-member ring 1-D pore channel as the largest pore channel, a structure with a 10-member ring 2-D pore channel as the largest pore channel, or a combination thereof. For the first oligomerization stage, a conventional oligomerization catalyst can be used, such as a solid acid catalyst.

The oligomerization catalyst in the first oligomerization stage can correspond to any convenient type of oligomerization catalyst, such as a zeotype or solid acid catalyst. A suitable zeotype framework can include a 10-member or 12-member ring pore channel network, such as a 1-dimensional 10-member ring pore channel or a 3-dimensional 10-member ring pore channel. Examples of suitable zeotypes having a 3-dimensional 10-member ring pore channel network include zeotypes having an MFI or MEL framework, such as ZSM-5 or ZSM-11. ZSM-5 is described in detail in U.S. Pat. Nos. 3,702,886 and Re. 29,948. ZSM-11 is described in detail in U.S. Pat. No. 3,709,979. Preferably, the zeolite is ZSM-5. Examples of suitable zeotypes having a 1-dimensional 10-member ring pore channel network include zeolites having a MRE (ZSM-48), MTW, TON, MTT, and/or MFS framework. In some aspects, a zeotype (such as a zeolite) with a 3-dimensional pore channel can be preferred for conversion of methanol, such as a zeotype with an MFI framework. In some aspects, a zeotype (such as a zeolite) with a 1-dimensional 10-member ring pore channel and/or a zeotype (such as a zeolite) with an MFI framework can be suitable for oligomerization of olefins. An example of a suitable oligomerization catalyst can include a zeolite with MRE (ZSM-48) framework. Other examples of suitable frameworks include, but are not limited to, MFI, MTW, MRE, TON, MTT, MWW, MOR, FAU, and BEA. More generally, potentially any framework structure including a 10-member ring or 12-member ring as the largest pore channel size can potentially be suitable. Additionally, mesoporous materials such as MCM-41 (and/or other M41S family materials) can also be suitable. Generally, a zeolite having desired activity for oligomerization of olefins can have a silicon to aluminum molar ratio of 20 to 100, or 30 to 80, or 40 to 70.

In some aspects, a zeolite in a catalyst can be present at least partly in the hydrogen form. Depending on the conditions used to synthesize the zeolite, this may correspond to converting the zeolite from, for example, the sodium form. This can readily be achieved, for example, by ion exchange to convert the zeolite to the ammonium form followed by calcination in air or an inert atmosphere at a temperature of 400° C. to 700° C. to convert the ammonium form to the active hydrogen form.

The solid acid (first stage) oligomerization catalyst can include and/or be enhanced by a transition metal. Preferably the transition metal is a Group 12 metal from the IUPAC periodic table (sometimes designated as Group IIB) selected from Zn, Cd, Ga or a combination thereof. More generally, the transition metal can be any convenient transition metal selected from Groups 6-15 of the IUPAC periodic table. The transition metal can be incorporated into the zeolite/catalyst by any convenient method, such as by impregnation, by ion exchange, by mulling prior to extrusion, and/or by any other convenient method. Optionally, the transition metal incorporated into a zeolite/catalyst can correspond to two or more metals. After impregnation or ion exchange, the transition metal-enhanced catalyst can be treated in air or an inert atmosphere at a temperature of 400° C. to 700° C. The amount of transition metal can be expressed as a weight percentage of metal relative to the total weight of the catalyst (including any zeolite and any binder). A catalyst can include 0.05 wt % to 20 wt % of one or more transition metals, or 0.1 wt % to 10 wt %, or 0.1 wt % to 5.0 wt %.

In some aspects, the distillate boiling range portion of the first stage oligomerization effluent can have a cetane rating of 42 or more, or 43 or more, and optionally up to 48 or more. The 371° C.+ portion can have a still higher cetane rating, such as at least 50, or at least 52, or at least 55, or at least 57. The aromatics content of the distillate boiling range portion can be 1.0 wt % or less, or 0.5 wt % or less, as determined by ASTM D5186.

Suitable and/or effective conditions for performing a (conventional) first stage oligomerization reaction can include average reactor temperatures of 125° C. to 250° C. (or 125° C. to 200° C., or 150° C. to 220° C.), total pressures between 100 psig (~0.7 MPa-g) to 2000 psig (~13.8 MPa-g), or 200 psig (~1.4 MPa-g) to 1000 psig (~6.9 MPa-g), or 70 psig (~500 kPa-g) to 180 psig (~1200 kPa-g) and an olefin space velocity between 0.1 $h^{-1}$ to 5 $h^{-1}$ based on weight of olefins relative to weight of catalyst. The lower pressure operating range for oligomerization can be beneficial for performing oligomerization on an olefin-containing portion of an oxygenate conversion effluent without having to perform prior compression on the portion of the conversion effluent. In some optional aspects, a small amount of oxygenate slip may occur, so that the input to the oligomerization stage includes 1.0 wt % or less of oxygenate that was not reacted during the oxygenate-to-olefin conversion. In such aspects, more frequent regeneration of the oligomerization catalyst may be desirable, such as a design where continuous regeneration of the oligomerization catalyst is performed.

In some aspects, an oligomerization process can be performed in two or more stages. Optionally, a multiple stage oligomerization process can be used as a reactive separator for separating $C_2$ olefins from $C_{3+}$ olefins. For example, a first oligomerization stage can be used to react a substantial portion (up to substantially all) of the $C_{3+}$ olefins in a feed, while reacting only a portion of the $C_2$ olefins. A separation can then be performed on this first oligomerized effluent to separate a fraction containing $C_2$ olefins from a fraction containing a majority of the oligomerized products from the first oligomerization stage. The fraction containing $C_2$ olefins can be used at least in part as a feed for the second oligomerization stage. The fraction containing $C_2$ olefins can include 60 wt % or more of olefins, or 80 wt % or more, and 5.0 wt % or less of $C_{3+}$ olefins.

In aspects where two or more oligomerization stages are used, both the first oligomerization stage and a second (or other subsequent) oligomerization stage can produce an oligomerized effluent that includes a lubricant boiling range portion. In such aspects, the viscosity index of the lubricant boiling range portion of the second oligomerization effluent can be greater than the viscosity index of the lubricant boiling range portion of the first oligomerization effluent by 10 or more, or 12 or more, or 15 or more. Without being boung by any particular theory, it is believed that the difference in the viscosity index for the lubricant boiling range portions of the first oligomerization effluent and the second oligomerization effluent reflects the high percentage of $C_2$ olefins used to form the oligomers in the second oligomerization stage. This results in a oligomers in the second oligomerization effluent that have a reduced number of branches and/or have a reduced chain length in the branches.

Example of Reaction System Configuration

Figure 1:
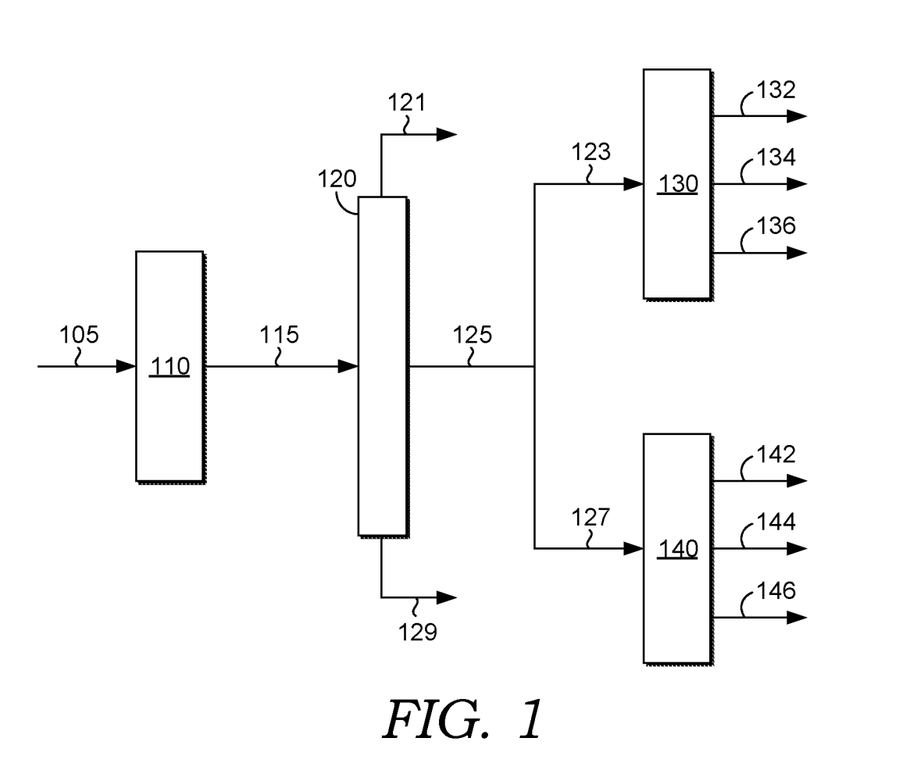
FIG. 1 schematically shows an example of a reaction system for conversion of oxygenates to distillate and lubricant boiling range products via intermediate conversion to light olefins.

FIG. 1 shows an example of a reaction system and process flow for conversion of a methanol feed into an olefin-containing feed, and subsequent oligomerization of the olefin-containing feed to form an oligomerized product including 50 wt % or more of a distillate boiling range fraction. In FIG. 1, an initial oxygenate feed 105 is passed into an oxygenate conversion stage 110. The oxygenate feed can correspond to a methanol and/or dimethyl ether feed, or the oxygenate feed can correspond to a mixture of oxygenates. The oxygenate conversion stage can include a catalyst for formation of light olefins, such as ZSM-48 or EMM-2. The oxygenate conversion stage 110 is shown as a single reactor in FIG. 1, but any convenient number of reactors in series or in parallel can be used. The oxygenate conversion stage 110 can generate a conversion effluent 115. The conversion effluent 115 can then (optionally) undergo one or more separations in a separation stage 120. The one or more separations can be used, for example, to separate an olefin-containing fraction 125 from the conversion effluent 115. This can also result in formation, for example, of a fraction containing water and/or carbon oxides 121 and a fraction containing heavier hydrocarbons 129. The olefin-containing fraction 125 can include 20 wt % to 90 wt % of $C_2$-$C_6$ olefins, based on a weight of hydrocarbons in the olefin-containing fraction.

The process flow in FIG. 1 shows a potential branching of olefin-containing fraction 125 into a stream containing $C_2$-$C_3$ olefins 123 and a stream containing $C_3$-$C_6$ olefins 127. In some aspects, this branching can represent the different types of olefin-containing fractions 125 that can be produced depending on the nature of the catalyst in oxygenate conversion stage 110. A catalyst such as ZSM-48 can be suitable for forming a stream similar to $C_3$-$C_6$ olefins stream 127, while a catalyst such as EMM-2 can be suitable for forming a stream similar to $C_2$-$C_3$ olefins stream 123. In other aspects, this branching can represent performing a separation to separate $C_2$-$C_3$ olefins stream 123 and $C_3$-$C_6$ olefins stream 127 from olefin-containing stream 125.

The $C_2$-$C_3$ olefins stream 123 and/or the $C_3$-$C_6$ olefins stream 127 can then be passed into the respective oligomerization stages 130 and 140. It is noted that the same type of oligomerization catalyst and the same type of reaction conditions can be used either in oligomerization stage 130 or oligomerization stage 140. The separate oligomerization stages are represented in FIG. 1 merely to illustrate the two different types of oligomerization reactions that may occur, depending on the nature of the olefins generated in oxygenate conversion stage 110. Oligomerization stage 130 can generate a naphtha boiling range product 132, a distillate fuel boiling range product 134, and a lubricant boiling range product 136. Similarly, oligomerization stage 140 can generate a naphtha boiling range product 142, a distillate fuel boiling range product 144, and a lubricant boiling range product 146.

Figure 2:
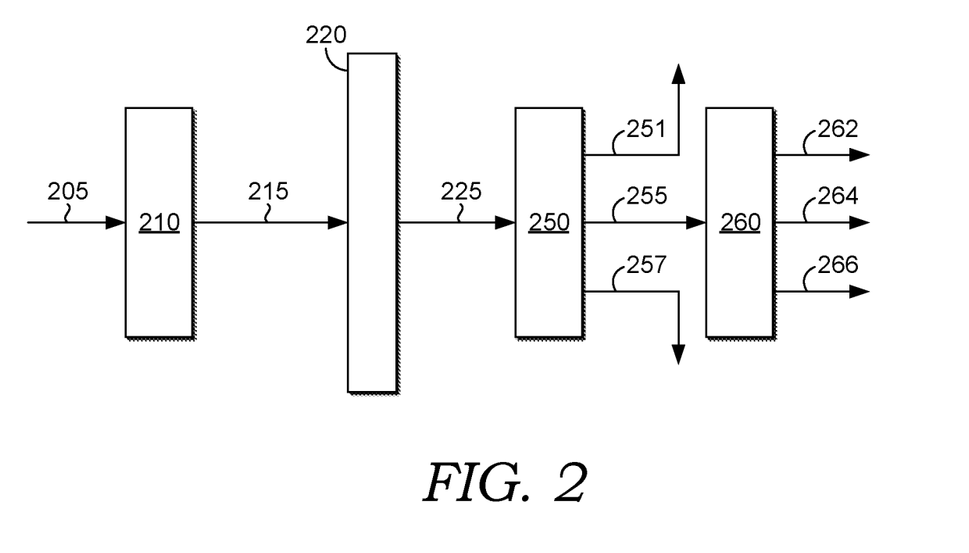
FIG. 2 schematically shows another example of a reaction system for conversion of oxygenates to distillate and lubricant boiling range products via intermediate conversion to light olefins.

FIG. 2 shows another type of process flow and process configuration that can be used for forming oligomerized products from an initial oxygenate feed. In FIG. 2, oxygenate feed 205 (such as a methanol and/or dimethyl ether feed) can be passed into oxygenate conversion stage 210. Similar to FIG. 1, the resulting conversion effluent 215 can be passed into a separation stage 220 to form an olefin-containing effluent 225, along with lighter products and heavier products. In FIG. 2, the olefin-containing effluent 225 can then be passed into a first oligomerization stage 250 that includes an oligomerization catalyst corresponding to a solid acid catalyst. The solid acid catalyst can optionally include one or more catalytic metals. In the example shown in FIG. 2, the first oligomerization stage produces one or more first heavy product streams 257 (such as a stream containing $C_{6+}$ aromatics), one or more water, carbon oxides, and other light ends streams 251, and a remaining first oligomerized effluent stream 255 that is enriched in $C_2$ olefins, due to selective reaction of the $C_{3+}$ olefins in the first oligomerization stage. Any separation stages used to separate first oligomerized product stream(s) 257 and water/light ends stream(s) 251 from the remaining portion of the first oligomerized effluent 255 are not shown in FIG. 2. The remaining portion of the first oligomerized effluent stream 255 is then passed into second oligomerization stage 260 for oligomerization in the presence of a Ni-enhanced zeotype catalyst as described herein, such as Ni-ZSM-48 or Ni-ZSM-57. The second oligomerization stage 260 can produce one or more naphtha product streams 262, one or more distillate fuel product streams 264, and one or more lubricant boiling range streams 266.

Example 1—Catalysts for Oligomerization

In the following examples, three catalysts were used for oligomerization of feeds containing $C_2$ to $C_4$ olefins. The three catalysts were each prepared in H- and Ni-forms.

The first type of catalyst was based on small crystal, self-bound MFI framework (ZSM-5) zeolite. The ZSM-5 had a silicon to aluminum ratio of roughly 65. After making an H-form extrudate of the self-bound zeolite, the Ni-ZSM-5 catalyst was made by spraying a solution of Ni(NO$_3$)$_2$ onto the catalyst in a rotary pill coater to load 1.0 wt % Ni onto the catalyst. The extrudates (either H-form or Ni-form) were then calcined in flowing air at 660° F. (~350° C.) for 3 hours to remove organic species before finally being sized to 14-25 mesh for reaction testing.

The second type of catalyst was a commercially produced MCM-41 catalyst with a silica to alumina ratio of roughly 45. The MCM-41 was co-extruded with an alumina binder (Versal-300) to form catalyst particles including roughly 35 wt % of binder. The extrudate was then calcined in flowing air at 660° F. (~350° C.) for 3 hours to remove organic species. For the Ni-containing MCM-41 catalyst, a solution of Ni(NO$_3$)$_2$ was sprayed onto the catalyst in a rotary pill coater to load 2.0 wt % Ni onto the catalyst. After addition of Ni, the Ni-MCM-41 was again calcined in flowing air at 660° F. (~350° C.) for 3 hours. The H-MCM-41 and Ni-MCM-41 catalysts were then sized to 14-25 mesh for reaction testing.

The third type of catalyst was a commercially available ZSM-48 crystal with a silica to alumina ratio of roughly 70. The ZSM-48 crystals were extruded in self-bound form. The extrudate was then calcined in flowing air at 660° F. (~350° C.) for 3 hours to remove organic species. For the Ni-containing ZSM-48 catalyst, a solution of Ni(NO$_3$)$_2$ was sprayed onto the catalyst in a rotary pill coater to load 2.0 wt % Ni onto the catalyst. After addition of Ni, the Ni-ZSM-48 was again calcined in flowing air at 660° F. (~350° C.) for 3 hours. The H-ZSM-48 and Ni-ZSM-48 catalysts were then sized to 14-25 mesh for reaction testing.

Example 2—Oligomerization with ZSM-48

The H-ZSM-48 and Ni-ZSM-48 catalysts from Example 1 were used for oligomerization of both mixed olefin feed and a feed containing ethylene as the only olefin. These feeds containing only $C_2$-$C_4$ olefins are representative of olefin feeds that could potentially be derived from a methanol conversion effluent (or other oxygenate conversion effluent) after conversion in the presence of a catalyst such as a ZSM-48 methanol conversion catalyst or an EMM-2 methanol conversion catalyst. Conventionally, the high content of small olefins from such methanol conversion catalysts would be viewed as a disadvantage feed, due to the relatively low amounts of aromatics made during the conversion. However, as shown below, oligomerization of such small olefin feeds can be unexpectedly beneficial when the oligomerization is performed using a Ni-ZSM-48 catalyst.

For oligomerization of the ethylene feed, a 100 wt % ethylene feed was exposed to the catalysts at 200° C., a weight hourly space velocity (WHSV) of 2.6 $h^{-1}$, and a pressure of 600 psig (~4.1 MPa-g). Under these conditions, the H-ZSM-48 catalyst did not convert any of the ethylene. By contrast, the Ni-ZSM-48 catalyst converted 99 wt % of the ethylene. Additionally, 72 wt % of the resulting hydrocarbons in the oligomerization product corresponded to 177° C.+ hydrocarbons. The 177° C.+ hydrocarbons corresponded to a mixture of distillate fuel boiling range components and lubricant boiling range components. Thus, Ni-ZSM-48 provided unexpectedly superior conversion of an ethylene feed that did not include other $C_{3+}$ olefins that might have facilitated oligomerization of the $C_2$ olefins.

The H-ZSM-48 and Ni-ZSM-48 were also exposed to a mixed olefin feed, as described in Example 3.

Example 3—Oligomerization of Mixed Olefin Feed

The catalysts from Example 1 were used for oligomerization of a mixed olefin feed. The mixed olefin feed included 10 wt % ethylene, 25 wt % propylene, 35 wt % butylene, and 30 wt % $N_2$. The mixed olefin feed was exposed to the catalysts at 200° C., a weight hourly space velocity (WHSV) of 1.66 $hr^{-1}$, and a pressure of 600 psig (~4.1 MPa-g). The total product generated by exposing the feed to each catalyst was subsequently hydrofinished and fractionated. Table 1 shows the amount of conversion for each type of olefin in the feed (based on analysis of the gas phase portion of the total product), along with the yield of 350° F.+ compounds (~177° C.+ compounds) relative to the weight of hydrocarbons in the feed.

TABLE 1

Mixed olefin conversion

| Catalyst | Ethylene Conv. (wt %) | Propylene Conv. (wt %) | Butylene Conv. (wt %) | 177° C.+ yield, wt % |
|---|---|---|---|---|
| H-ZSM-48 | 51% | 99% | 99% | 83% |
| Ni-ZSM-48 | 65% | 99% | 95% | 74% |
| H-ZSM-5 | 46% | 60% | 99% | 63% |
| Ni-ZSM-5 | 41% | 54% | 97% | 63% |
| H-MCM-41 | 0% | 69% | 62% | 39% |
| Ni-MCM-41 | 72% | 85% | 83% | 37% |

As illustrated in Example 2 and further shown in Table 1, addition of nickel to a catalyst provides an unexpected increase in the amount of ethylene conversion. However, addition of Ni to ZSM-48 provides a range of additional unexpected benefits relative to the other catalysts. With regard to the conversion and yield results shown in Table 1, addition of Ni to MCM-41 did result in additional conversion of the mixed olefin feed. However, due to the relatively low conversion for H-MCM-41, the resulting increase in conversion for Ni-MCM-41 was still substantially lower than the amount of conversion provided by Ni-ZSM-48. For Ni-ZSM-5, addition of Ni did not appear to provide increased conversion or yield relative to H-ZSM-5. Thus, the ZSM-48 catalysts provide the highest overall amounts of conversion of olefins and highest yields of distillate product, with Ni-ZSM-48 providing the highest overall conversion.

The 177° C.+ products shown in Table 1 were further fractionated to form a 177° C. to 360° C. (roughly 350° F. to 680° F.) portion, a 360° C. to 455° C. portion (roughly 680° F. to 850° F.), and a 455° C.+ portion. The 177° C. to 360° C. portion corresponds to a distillate fuel boiling range product. The 360° C. to 455° C. roughly corresponds to a light neutral base stock product. The 455° C.+ portion roughly corresponds to a heavy neutral base stock product. Table 2 shows the yields of each portion. The yields in Table 2 add to the total yield value shown in Table 1 for each catalyst.

TABLE 2

Relative Product Yields

| Catalyst | Distillate Fuel Yield | Light Neutral Yield | Heavy Neutral Yield |
|---|---|---|---|
| H-ZSM-48 | 63% | 17% | 3% |
| Ni-ZSM-48 | 62% | 11% | 1% |
| H-ZSM-5 | 58% | 5% | 0% |
| Ni-ZSM-5 | 54% | 7% | 2% |
| H-MCM-41 | 38% | 1% | 0% |
| Ni-MCM-41 | 35% | 2% | 0% |

Table 2 shows that the ZSM-48 catalysts unexpectedly provided the highest overall yields while also providing a heavy neutral product.

Some of the distillate fuel, light neutral, and heavy neutral portions were further characterized for cetane rating and aromatics content (for the distillate fuel product) and viscosity index (for the lubricant boiling range products). Table 3 shows the results of this additional characterization. In addition to the results shown in Table 3, it is noted that all of the distillate fractions had aromatics contents of less than 1.0 wt %.

TABLE 3

Product Characterization

| Catalyst | Distillate Cetane | Light Neutral VI | Heavy Neutral VI |
|---|---|---|---|
| H-ZSM-48 | 46.5 | 87.7 | 89.2 |
| Ni-ZSM-48 | 48.7 | 96.6 | |
| H-ZSM-5 | | 45.6 | |
| Ni-ZSM-5 | | | |
| H-MCM-41 | | | |
| Ni-MCM-41 | 29.9 | | |

As shown in Table 3, the ZSM-48 catalysts provided unexpectedly superior distillate fuel and lubricant properties. With regard to H-ZSM-48 relative to Ni-ZSM-48, it is noted that Table 2 shows that H-ZSM-48 provided the highest yield value for 177° C.+ products. However, Table 3 shows that exposure of the mixed olefin feed to Ni-ZSM-48 resulted in unexpectedly improved product qualities. For example, the Ni-ZSM-48 catalyst had an unexpectedly higher cetane index (for the distillate fuel portion) and an unexpectedly high viscosity index (for the light neutral portion) in comparison with the products from the H-ZSM-48 catalyst. This improvement in product quality is counter-intuitive in view of the reduced 177° C.+ yield provided by Ni-ZSM-48 relative to H-ZSM-48.

Example 4—Oligomerization of Ethylene Feed

The catalysts from Example 1 were also used for oligomerization of a 100% ethylene feed. The ethylene feed was exposed to the catalysts at 200° C., a WHSV of 2.6 h$^{-1}$, and a pressure of 600 psig (~4.1 MPa-g). Table 4 shows the ethylene conversion and resulting 177° C.+ yield. In Table 4, the 177° C.+ yield is relative to the amount of ethylene converted.

TABLE 4

Ethylene Conversion and Yield

| Catalyst | Ethylene Conversion (wt %) | 177° C.+ yield (wt %) |
|---|---|---|
| H-ZSM-48 | 0% | |
| Ni-ZSM-48 | 99% | 72% |
| H-ZSM-5 | 0% | |
| Ni-ZSM-5 | 17% | 71% |
| H-MCM-41 | 0% | |
| Ni-MCM-41 | 93% | 34% |

Under the reaction conditions for Table 4, none of the H-form catalysts were effective for ethylene conversion. By contrast, the Ni-form catalysts all had at least some effectiveness for ethylene conversion. However, the Ni-ZSM-5 catalyst rapidly deactivated, so that the 17% yield was only available for a short period. The Ni-MCM-41 catalyst was effective for converting the ethylene, but only roughly a third of the product corresponded to a distillate fuel or lubricant boiling range product. By contrast, the Ni-ZSM-48 catalyst provided an unexpectedly superior combination of ethylene conversion and distillate/lubricant yield.

The total liquid product from the Ni-form catalysts was fractionated and further analyzed. The 177° C.+ portion of the total product was fractionated to form a 177° C.-360° C. fraction (distillate fuel fraction), a 360° C.-455° C. fraction (light neutral fraction), and a 455° C.+ fraction (heavy neutral fraction). Table 5 shows the respective yield of the distillate fuel, light neutral, and heavy neutral fractions within the 177° C.+ portion of the total product.

TABLE 5

Relative Product Yields (wt %)

| | Distillate fuel yield | Light Neutral yield | Heavy Neutral yield |
|---|---|---|---|
| Ni-ZSM-48 | 60% | 10% | 2% |
| Ni-ZSM-5 | 61% | 9% | 1% |
| Ni-MCM-41 | 32% | 1% | 1% |

As shown in Table 5, the Ni-ZSM-48 and Ni-ZSM-5 catalysts provided substantially higher yields of distillate and lubricant boiling range products. However, as shown in Table 4, Ni-ZSM-5 quickly became deactivated under the reaction conditions, resulting in incomplete conversion of the ethylene feed. By contrast, Ni-ZSM-48 was able to maintain activity. Thus, Ni-ZSM-48 provides an unexpectedly beneficial combination of providing high conversion for ethylene feeds (such as feeds that have reduced or minimized contents of $C_{3+}$ olefins), maintaining activity while oligomerizing ethylene feeds, and producing a product slate including a substantial lubricant boiling range portion.

The unexpected benefits of Ni-ZSM-48 are further illustrated in Table 6, which shows additional characterization details for the resulting distillate fuel boiling range portion and light neutral boiling range portion of the products.

TABLE 6

Product Characterization

| | Distillate Cetane | Total Aromatics | Light Neutral VI |
|---|---|---|---|
| Ni-ZSM-48 | 47.1 | <1 wt % | 112 |
| Ni-ZSM-5 | 43.7 | <1 wt % | |
| Ni-MCM-41 | 39.7 | <1 wt % | |

As shown in Table 6, the distillate fuel boiling range portion of the oligomerization effluent from Ni-ZSM-48 provided an unexpectedly higher cetane index than the distillate fuel boiling range portions of the effluents from the other catalysts.

Additional Embodiments

Embodiment 1

A method for conversion of oxygenates, comprising: exposing a feed comprising one or more oxygenates to an oxygenate conversion catalyst under conditions for producing an olefin-containing effluent, the olefin-containing effluent comprising 60 wt % or more of $C_3$-$C_6$ olefins and 10 wt % or less aromatics relative to a weight of hydrocarbons in the olefin-containing effluent, a ratio of $C_5$-$C_6$ olefins versus $C_4$ olefins in the olefin-containing effluent being 1.0 or more, the methanol conversion catalyst comprising a zeotype framework structure having a largest pore channel corresponding to a 10-member ring pore channel; separating a light olefin effluent from the olefin-containing effluent, the light olefin effluent comprising 70 wt % or more total olefins relative to a weight of hydrocarbons in the light olefin effluent; and exposing at least a portion of the light olefin effluent to an oligomerization catalyst comprising Ni supported on a support comprising a zeotype framework structure having 1-D 10-member ring pore channels under oligomerization conditions to form an oligomerized effluent, the at least a portion of the light olefin effluent comprising 5 wt % or more ethylene relative to a weight of olefins in the at least a portion of the light olefin effluent, wherein the oligomerization conditions comprise conversion of 50 wt % or more of the ethylene in the at least a portion of the light olefin effluent.

Embodiment 2

The method of Embodiment 1, wherein the olefin-containing effluent comprises 40 wt % or more of $C_4$-$C_6$ olefins.

Embodiment 3

The method of any of the above embodiments, wherein the one or more oxygenates comprise 50 wt % or more (or 75 wt % or more, or 90 wt % or more) of methanol, dimethyl ether, or a combination thereof.

Embodiment 4

The method of any of the above embodiments, wherein the light olefin effluent comprises 80 wt % or more $C_3$-$C_6$ olefins relative to a weight of olefins in the light olefin effluent.

Embodiment 5

The method of any of the above embodiments, wherein the methanol conversion catalyst comprises a zeotype framework structure including a 10-member, 1-D pore channel as the largest pore channel in the framework structure, the methanol conversion catalyst optionally comprising ZSM-48.

Embodiment 6

The method of any of the above embodiments, wherein the oligomerization conditions comprise conversion of 70 wt % or more (or 90 wt % or more) of the ethylene in the at least a portion of the light olefin effluent.

Embodiment 7

The method of any of the above embodiments, wherein the oligomerized effluent comprises a yield of 55 wt % or more of distillate fuel boiling range hydrocarbons relative to a total weight of hydrocarbons in the at least a portion of the light olefin fraction, or wherein the oligomerized effluent comprises a yield of 10 wt % or more of lubricant boiling range hydrocarbons, or a combination thereof.

Embodiment 8

The method of Embodiment 7, wherein the distillate fuel boiling range compounds have a cetane index of 40 or more (or 42 or more), or wherein a 360° C. to 455° C. portion of the lubricant boiling range hydrocarbons has a viscosity index of 85 or more (or 90 or more), or a combination thereof.

Embodiment 9

The method of any of the above embodiments, wherein the oligomerized effluent comprises a yield of 35 wt % or less of naphtha boiling range compounds relative to a total weight of hydrocarbons in the at least a portion of the light olefin fraction (or 25 wt % or less).

Embodiment 10

The method of any of the above embodiments, wherein the oligomerization catalyst comprises 0.1 wt % to 10 wt % Ni supported on a support comprising an MRE framework structure, an MFS framework structure, a zeotype framework structure including a 10-member ring, 1-D pore channel as the largest pore channel in the framework structure, a zeotype framework structure including a 10-member ring, 2-D pore channel as the largest pore channel, ZSM-48, ZSM-57, or a combination thereof.

Embodiment 11

The method of any of the above embodiments, wherein the oligomerization catalyst comprises 0.1 wt % to 10 wt % Ni supported on a support comprising ZSM-48.

Embodiment 12

The method of any of the above embodiments, wherein exposing at least a portion of the light olefin effluent to an oligomerization catalyst comprises: exposing at least a portion of the light olefin effluent to a first oligomerization catalyst comprising a solid acid catalyst having zeotype framework structure under first oligomerization conditions to form a first oligomerized effluent, the at least a portion of the light olefin effluent comprising 10 wt % or more ethylene relative to a weight of olefins in the at least a portion of the light olefin effluent, a weight of $C_2$ olefins in the first oligomerized effluent being 50 wt % or more of a weight of $C_2$ olefins in the light olefin effluent; and exposing at least a portion of the first oligomerized effluent to a second oligomerization catalyst comprising Ni supported on a support comprising a zeotype framework structure having 1-D 10-member ring pore channels under second oligomerization conditions to form a second oligomerized effluent, wherein the second oligomerization conditions comprise conversion of 50 wt % or more of the ethylene in the at least a portion of the first oligomerization effluent.

Embodiment 13

The method of Embodiment 12, wherein the second oligomerization catalyst comprises 0.1 wt % to 10 wt % Ni supported on a support comprising ZSM-48.

Embodiment 14

An oligomerization effluent formed according to the method of any of Embodiments 1-13.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A method for conversion of oxygenates, comprising:
exposing a feed comprising one or more oxygenates to an oxygenate conversion catalyst under conditions for producing an olefin-containing effluent, the olefin-containing effluent comprising 60 wt % or more of $C_3$-$C_6$ olefins and 10 wt % or less aromatics relative to a weight of hydrocarbons in the olefin-containing effluent, a ratio of $C_5C_6$ olefins versus $C_4$ olefins in the olefin-containing effluent being 1.0 or more, the oxygenate conversion catalyst comprising a zeotype framework structure having a largest pore channel corresponding to a 10-member ring pore channel;
separating a light olefin effluent from the olefin-containing effluent, the light olefin effluent comprising 70 wt % or more total olefins relative to a weight of hydrocarbons in the light olefin effluent; and exposing at least a portion of the light olefin effluent to an oligomerization catalyst comprising Ni supported on a support comprising a zeotype framework structure having 1-D 10-member ring pore channels under oligomerization conditions to form an oligomerized effluent comprising distillate fuel boiling range hydrocarbons, lubricant boiling range hydrocarbons, or a combination thereof, the at least a portion of the light olefin effluent comprising 5.0 wt % or more ethylene relative to a weight of olefins in the at least a portion of the light olefin effluent, wherein the oligomerization conditions comprise conversion of 50 wt % or more of the ethylene in the at least a portion of the light olefin effluent.

2. The method of claim 1, wherein the olefin-containing effluent comprises 40 wt % or more of $C_4$-$C_6$ olefins.

3. The method of claim 1, wherein the one or more oxygenates comprise 50 wt % or more of methanol, dimethyl ether, or a combination thereof.

4. The method of claim 1, wherein the light olefin effluent comprises 80 wt % or more $C_3$-$C_6$ olefins relative to a weight of olefins in the light olefin effluent.

5. The method of claim 1, wherein the oxygenate conversion catalyst comprises a zeotype framework structure including a 10-member, 1-D pore channel as the largest pore channel in the framework structure.

6. The method of claim 5, wherein the oxygenate conversion catalyst comprises ZSM-48.

7. The method of claim 1, wherein the oligomerization conditions comprise conversion of 70 wt % or more of the ethylene in the at least a portion of the light olefin effluent.

8. The method of claim 1, wherein the oligomerized effluent comprises a yield of 55 wt % or more of distillate fuel boiling range hydrocarbons relative to a total weight of hydrocarbons in the at least a portion of the light olefin fraction, or wherein the oligomerized effluent comprises a yield of 10 wt % or more of lubricant boiling range hydrocarbons, or a combination thereof.

9. The method of claim 8, wherein the distillate fuel boiling range compounds have a cetane index of 40 or more.

10. The method of claim 8, wherein a 360° C. to 455° C. portion of the lubricant boiling range hydrocarbons has a viscosity index of 85 or more.

11. The method of claim 1, wherein the oligomerized effluent comprises a yield of 35 wt % or less of naphtha boiling range compounds relative to a total weight of hydrocarbons in the at least a portion of the light olefin fraction.

12. The method of claim 1, wherein the oligomerization catalyst comprises 0.1 wt % to 10 wt % Ni supported on a support comprising an MRE framework structure, a zeotype framework structure including a 10-member ring, 1-D pore channel as the largest pore channel in the framework structure, or a combination thereof.

13. The method of claim 1, wherein the oligomerization catalyst comprises 0.1 wt % to 10 wt % Ni supported on a support comprising ZSM-48.

14. A method for conversion of oxygenates, comprising:

exposing a feed comprising one or more oxygenates to an oxygenate conversion catalyst under conditions for producing an olefin-containing effluent, the olefin-containing effluent comprising 60 wt % or more of $C_3$-$C_6$ olefins and 10 wt % or less aromatics relative to a weight of hydrocarbons in the olefin-containing effluent, a ratio of $C_5$-$C_6$ olefins versus $C_4$ olefins in the olefin-containing effluent being 1.0 or more, the oxygenate conversion catalyst comprising a zeotype framework structure having a largest pore channel corresponding to a 10-member ring pore channel;

separating a light olefin effluent from the olefin-containing effluent, the light olefin effluent comprising 70 wt % or more total olefins relative to a weight of hydrocarbons in the light olefin effluent;

exposing at least a portion of the light olefin effluent to a first oligomerization catalyst comprising a solid acid catalyst having zeotype framework structure under first oligomerization conditions to form a first oligomerized effluent, the at least a portion of the light olefin effluent comprising 10 wt % or more ethylene relative to a weight of olefins in the at least a portion of the light olefin effluent, a weight of $C_2$ olefins in the first oligomerized effluent being 50 wt % or more of a weight of $C_2$ olefins in the light olefin effluent; and exposing at least a portion of the first oligomerized effluent to a second oligomerization catalyst comprising Ni supported on a support comprising a zeotype framework structure having 1-D 10-member ring pore channels under second oligomerization conditions to form a second oligomerized effluent comprising distillate fuel boiling range hydrocarbons, lubricant boiling range hydrocarbons, or a combination thereof, wherein the second oligomerization conditions comprise conversion of 50 wt % or more of the ethylene in the at least a portion of the first oligomerization effluent.

15. The method of claim 14, wherein the second oligomerization catalyst comprises 0.1 wt % to 10 wt % Ni supported on a support comprising ZSM-48.

16. The method of claim 1, wherein the one or more oxygenates comprise 75 wt % or more of methanol, dimethyl ether, or a combination thereof.

17. The method of claim 1, wherein the second oligomerization conditions comprise conversion of 70 wt % or more of the ethylene in the at least a portion of the light olefin effluent.

* * * * *